(12) United States Patent
Tappehorn et al.

(10) Patent No.: US 12,036,368 B2
(45) Date of Patent: Jul. 16, 2024

(54) TRANSFER UNIT, VENTILATOR, VENTILATION SYSTEM, PROCESS FOR CHANGING A VENTILATOR USED FOR A VENTILATION PROCESS OF A PATIENT

(71) Applicant: Drägerwerk AG & Co. KGaA, Lübeck (DE)

(72) Inventors: Ludger Tappehorn, Lübeck (DE); Erwin Broos, Ratekau (DE); Birger Landwehr, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1093 days.

(21) Appl. No.: 16/667,425

(22) Filed: Oct. 29, 2019

(65) Prior Publication Data

US 2020/0129721 A1    Apr. 30, 2020

(30) Foreign Application Priority Data

Oct. 30, 2018   (DE) ..................... 10 2018 008 493.1

(51) Int. Cl.
*A61M 16/00*       (2006.01)
*A61M 16/08*       (2006.01)
(Continued)

(52) U.S. Cl.
CPC .... *A61M 16/0816* (2013.01); *A61M 16/0003* (2014.02); *A61M 16/024* (2017.08);
(Continued)

(58) Field of Classification Search
CPC .. A61M 2039/1016; A61M 2039/1022; A61M 2205/502; A61M 16/0003;
(Continued)

(56) References Cited

U.S. PATENT DOCUMENTS 4,323,064 A * 4/1982 Hoenig ................. A61M 16/00
128/205.24
5,918,597 A * 7/1999 Jones .................... A61M 16/00
128/204.26
(Continued)

FOREIGN PATENT DOCUMENTS

CA        2977709 C  *  3/2020  ........ A61M 16/0003
DE    102007019487 B3    4/2008
(Continued)

*Primary Examiner* — Michael R Reid
*Assistant Examiner* — Tyler A Raubenstraw
(74) *Attorney, Agent, or Firm* — McGlew and Tuttle, P.C.

(57) ABSTRACT

A transfer unit (20), for a ventilator (1), is provided for carrying out a ventilation process of a patient. A ventilator (1) for carrying out a ventilation process of a patient, is provided that includes a ventilation unit (10) with a pneumatic unit (16) for carrying out the ventilation process as well as the transfer unit (20) mounted reversibly at the ventilation unit (10). A ventilation system (100) for carrying out a ventilation process of a patient, is provided including a transfer unit (20) and at least two ventilation units (10). A process for changing a ventilator (1) is provided for the ventilation process of a patient, wherein the transfer unit (20) can be mounted in the ventilation system (100) at a first ventilation unit (10) for forming a first ventilator (1) and at a second ventilation unit (10) for forming a second ventilator (1).

22 Claims, 8 Drawing Sheets

(51) Int. Cl.
*A61M 16/20* (2006.01)
*A61M 39/10* (2006.01)

(52) U.S. Cl.
CPC ...... *A61M 16/208* (2013.01); *A61M 39/1011* (2013.01); *A61M 2039/1016* (2013.01); *A61M 2039/1022* (2013.01); *A61M 2205/0272* (2013.01); *A61M 2205/3341* (2013.01); *A61M 2205/502* (2013.01); *A61M 2205/52* (2013.01)

(58) Field of Classification Search
CPC .............. A61M 16/024; A61M 16/208; A61M 2205/3341; A61M 2205/52; A61M 16/0816; A61M 39/1011; A61M 2205/0272; A61M 16/205
See application file for complete search history.

(56) References Cited

U.S. PATENT DOCUMENTS

| | | | | |
|---|---|---|---|---|
| 8,656,915 | B2 * | 2/2014 | Bayron | A61M 16/209 128/205.24 |
| 11,433,209 | B2 * | 9/2022 | Geraci | A61M 16/0816 |
| 2008/0091117 | A1 * | 4/2008 | Choncholas | A61M 16/12 128/204.23 |
| 2008/0264417 | A1 * | 10/2008 | Manigel | A61M 16/0063 128/205.12 |
| 2010/0078024 | A1 * | 4/2010 | Andrieux | A61M 16/201 128/204.21 |
| 2010/0139660 | A1 * | 6/2010 | Adahan | A61M 16/206 128/205.24 |
| 2010/0229867 | A1 * | 9/2010 | Bertinetti | A61M 16/0051 345/184 |
| 2011/0132369 | A1 * | 6/2011 | Sanchez | A61M 16/0051 128/204.23 |
| 2011/0259333 | A1 * | 10/2011 | Sanchez | A61M 16/0051 345/1.3 |
| 2011/0315139 | A1 * | 12/2011 | Mashak | A61M 16/01 128/203.14 |
| 2012/0145154 | A1 * | 6/2012 | Baloa Welzien | A61B 5/08 128/204.23 |
| 2012/0204875 | A1 * | 8/2012 | Brazy | A61M 16/024 128/204.22 |
| 2013/0092167 | A1 * | 4/2013 | Perlman | A61M 16/024 128/205.24 |
| 2013/0167842 | A1 * | 7/2013 | Jafari | A61M 16/0003 128/204.21 |
| 2013/0263854 | A1 * | 10/2013 | Taylor | A61M 16/125 128/204.23 |
| 2013/0312746 | A1 * | 11/2013 | Grychowski | A61M 16/0866 128/203.14 |
| 2014/0246025 | A1 * | 9/2014 | Cragg | A61M 16/0866 128/204.19 |
| 2014/0283829 | A1 * | 9/2014 | Miller | A61B 5/01 128/203.14 |
| 2014/0332003 | A1 * | 11/2014 | Crumblin | A61B 5/0245 128/203.12 |
| 2015/0107593 | A1 * | 4/2015 | Truschel | A61M 16/0069 128/204.22 |
| 2015/0114395 | A1 * | 4/2015 | Heinonen | A61M 16/12 128/204.23 |
| 2015/0122259 | A1 * | 5/2015 | Fox | A61M 16/0096 128/204.19 |
| 2015/0165146 | A1 * | 6/2015 | Bowman | A61M 16/16 128/203.14 |
| 2015/0290408 | A1 * | 10/2015 | Bonassa | A61M 16/205 128/204.23 |
| 2015/0314090 | A1 * | 11/2015 | Wu | A61M 16/0003 128/202.22 |
| 2016/0058967 | A1 * | 3/2016 | McCormick | A61M 16/0883 128/205.24 |
| 2016/0151590 | A1 * | 6/2016 | Porcyk | A61M 16/0069 128/204.23 |
| 2016/0202890 | A1 * | 7/2016 | Feldhahn | A61M 16/024 715/771 |
| 2016/0235932 | A1 * | 8/2016 | Rankin | A61M 16/0075 |
| 2016/0310689 | A1 * | 10/2016 | Osborne | A61M 39/12 |
| 2017/0151411 | A1 * | 6/2017 | Osborne | G01K 1/08 |
| 2017/0209662 | A1 * | 7/2017 | Ahmad | A61M 16/107 |
| 2017/0312464 | A1 * | 11/2017 | Robitaille | A61M 16/0081 |
| 2018/0133418 | A1 * | 5/2018 | Brand | A61M 16/0006 |
| 2018/0243527 | A1 * | 8/2018 | Zapol | A61M 16/107 |
| 2018/0243528 | A1 * | 8/2018 | Zapol | C01B 21/32 |
| 2018/0280646 | A1 * | 10/2018 | Freeman | A61M 16/024 |
| 2018/0339120 | A1 * | 11/2018 | Vicario | A61M 16/0003 |
| 2018/0344918 | A1 * | 12/2018 | Turner | A61G 10/023 |
| 2019/0015614 | A1 * | 1/2019 | Alahmadi | A61B 5/082 |
| 2019/0099571 | A1 * | 4/2019 | Shelly | A61B 5/4848 |
| 2019/0274633 | A1 * | 9/2019 | Kuzelka | A61B 5/746 |
| 2020/0016350 | A1 * | 1/2020 | Heinonen | G16H 50/70 |
| 2020/0078547 | A1 * | 3/2020 | Thiessen | A61M 16/024 |
| 2020/0282163 | A1 * | 9/2020 | Schranz | A61M 16/0003 |
| 2021/0187219 | A1 * | 6/2021 | Lychou | A61M 16/00 |

FOREIGN PATENT DOCUMENTS

| | | | | |
|---|---|---|---|---|
| EP | | 938909 A1 * | 9/1999 | .......... A61M 16/024 |
| EP | | 0938909 A1 | 9/1999 | |
| WO | WO-9003820 A1 * | | 10/1988 | ............ A61M 16/01 |
| WO | WO-2012139159 A1 * | | 10/2012 | ............ A61M 16/00 |
| WO | WO-2014210566 A2 * | | 12/2014 | ........ A61M 16/0051 |
| WO | WO-2016087859 A1 * | | 6/2016 | .......... A61M 1/1601 |

* cited by examiner

TRANSFER UNIT, VENTILATOR, VENTILATION SYSTEM, PROCESS FOR CHANGING A VENTILATOR USED FOR A VENTILATION PROCESS OF A PATIENT

CROSS REFERENCE TO RELATED APPLICATIONS

This application claims the benefit of priority under 35 U.S.C. § 119 of German Patent Application 10 2018 008 493.1, filed Oct. 30, 2018, the entire contents of which are incorporated herein by reference.

TECHNICAL FIELD

The present invention pertains to a transfer unit for a ventilator (also known as a respirator) for carrying out a ventilation process of a patient, the transfer unit having a breathing air section for guiding a breathing air, an exhaled air section for guiding exhaled air as well as a mounting section for reversible mounting at a counter-mounting section of a ventilation unit of the ventilator, the exhaled air section having a patient inhalation port for fluid-communicating connection to a counter-patient inhalation port of a ventilation tube element and a ventilation inhalation port for fluid-communicating connection to a counter-ventilation inhalation port of the ventilation unit, the exhaled air section having a patient exhalation port for fluid-communicating connection to a counter-patient exhalation port of the ventilation tube element and a ventilation exhalation port for fluid-communicating connection to a counter-ventilation exhalation port of the ventilation unit.

The present invention further pertains to a ventilator for carrying out a ventilation process of a patient, having a ventilation unit with a pneumatic unit for carrying out the ventilation process, a transfer unit mounted reversibly at the ventilation unit as well as a control unit for the controlled operation of the pneumatic unit, wherein a mounting section of the transfer unit is mounted reversibly at a counter-mounting section of the ventilation unit, wherein a ventilation inhalation port of the transfer unit is further connected in a fluid-communicating manner to a counter-ventilation inhalation port of the ventilation unit, wherein a ventilation exhalation port of the transfer unit is further connected in a fluid-communicating manner to a counter-ventilation exhalation port of the ventilation unit.

Furthermore, the present invention pertains to a ventilation system for carrying out a ventilation process of a patient, comprising a transfer unit and at least two ventilation units, the at least two ventilation units having each at least one pneumatic unit for carrying out the ventilation process, a counter-mounting section for the reversible mounting of a mounting section of the transfer unit, a counter-ventilation inhalation port for fluid-communicating connection to a ventilation inhalation port of the transfer unit as well as a counter-ventilation exhalation port for fluid-communicating connection to a ventilation exhalation port of the transfer unit.

In another aspect, the present invention pertains to a process for changing a ventilator used for a ventilation process of the patient in a ventilation system, wherein the transfer unit can be mounted at a first ventilation unit to form a first ventilator and at a second ventilation unit to form a second ventilator, and wherein the ventilation process is carried out at the beginning of the process by the first ventilator.

TECHNICAL BACKGROUND

It is generally known in the medical care of patients that a patient is ventilated mechanically, if necessary, by a ventilator of a ventilation system or a spontaneous breathing of the patient is at least assisted, if possible, by a ventilator. This so-called ventilation process is usually determined by a plurality of ventilation parameters, which can be set especially by an operating staff of the ventilator, for example, physicians and/or nursing staff. It may often happen during a treatment of a patient that it is necessary to transport a patient being ventilated in this manner within the hospital or even to transfer the patient to another hospital. It must be ensured in such a case that the ventilation of the patient is not compromised or is only compromised insignificantly during the transport.

It is known, in particular, according to the state of the art that transfer units can be used, which may be mounted at different ventilation units, in order to form with these a ventilator as a unit. Preparations can be made in this manner, for example, for a transition from a ventilation of the patient by a stationary ventilator to a ventilation of the patient by a mobile ventilator.

Such transfer units, ventilation units and combined ventilators are known, for example, from US 2016 058 967 A1. It was, however, found to be disadvantageous in this connection that ventilation of the patient is interrupted during the transfer process of the transfer unit from one ventilation unit to the next one, because the breathing air and the exhaled air of the patient are short-circuited internally in the transfer unit.

Further, similar transfer units, ventilation units and combined ventilators are known, for example, from EP 0 938 909 A1. However, the ventilation process of the patient is also interrupted, especially in an uncontrolled manner, according to this embodiment during a transfer of the transfer unit between the ventilation units. For example, a positive end-expiratory pressure, which describes especially the pressure of the breathing air that remains in the lungs of the patient at the end of an exhalation process, cannot thus be maintained in this embodiment during a transfer of the transfer unit. However, such a positive end-expiratory pressure (PEEP) makes it especially possible to prevent a collapse of lung regions, which may prove to be problematic during a further subsequent ventilation. Even though collapsed lung regions can often be made accessible for ventilation by special maneuvers, for example, by ventilation with increased ventilation pressure, these maneuvers usually represent a great burden for the patient. If these special maneuvers are not successful, the collapsed lung regions are no longer available in the worst case for a ventilation of the patient.

SUMMARY

A basic object of the present invention is to improve a transfer unit, a ventilator, a ventilation system as well as a process for changing a ventilator used for a ventilation process of a patient. An object of the present invention is, in particular, to provide a transfer unit for a ventilator, a ventilator for carrying out a ventilation process, a ventilation system for carrying out a ventilation process as well as a process for changing a ventilator used for a ventilation process of a patient, which improve a change of a ventilator used for a ventilation process of the patient in an especially simple and cost-effective manner, wherein it is possible, in particular, to make possible an at least partial, preferably independent breathing of the patient, and, in particular, a minimum pressure of the exhaled air of the patient can be maintained, especially preferably for providing a constant or at least essentially constant positive end-expiratory pressure during the change of the ventilator.

The above object is accomplished by a transfer unit for a ventilator according to the invention, by a ventilator for carrying out a ventilation process of a patient with the transfer unit, by a ventilation system for carrying out a ventilation process of a patient with the transfer unit, as well as by a process for charging a ventilator used for a ventilation process of a patient with the transfer unit. Features and details that are described in connection with the transfer unit according to the present invention, do, of course, also apply in connection with the ventilator according to the present invention, with the ventilation system according to the present invention as well as with the process according to the present invention and also vice versa, so that reference is and can always mutually be made to the individual aspects of the present invention concerning the disclosure.

According to a first aspect of the present invention, the object is accomplished by a transfer unit for a ventilator for carrying out a ventilation process of a patient, the transfer unit having a breathing air section for guiding a breathing air, an exhaled air section for guiding an exhaled air as well as a mounting section for reversible mounting on a counter-mounting section of a ventilation unit of the ventilator, the exhaled air section having a patient inhalation port for fluid-communicating connection to a counter-patient inhalation port of a ventilation tube element and a ventilation inhalation port for fluid-communicating connection to a counter-ventilation inhalation port of the ventilation unit, the exhaled air section having a patient exhalation port for fluid-communicating connection to a counter-patient exhalation port of the ventilation tube element and a ventilation exhalation port for fluid-communicating connection to a counter-exhalation port for fluid-communicating connection to a counter-ventilation exhalation port of the ventilation unit. A transfer unit according to the present invention is characterized in that a breathing valve with a first nonreturn device for securing a flow of breathing air with a breath flow direction from the ventilation inhalation port to the patient inhalation port is mounted in the breathing air section as well as an exhalation valve with a second nonreturn device for securing a flow of exhaled air with an exhalation flow direction from the patient exhalation port to the ventilation exhalation port is mounted in the exhaled air section, wherein the exhalation valve has a minimum pressure device for securing a minimum pressure of the exhaled air at least in the exhaled air section.

The mounting section preferably has at least one coupling element for connecting a ventilation tube element, especially a ventilation tube. The counter-mounting section preferably also has at least one coupling element for connecting a ventilation tube element, especially a ventilation tube. The transfer unit and the ventilation unit can be connected to one another in this manner in a fluid-communicating manner via ventilation tubes. Exhalation means breathing out in the sense of the application, i.e., a gas flow away from the patient. Inhalation correspondingly means breathing in in the sense of the present invention, i.e., a gas flow towards the patient. A patient inhalation port is preferably an inspiratory patient port of the transfer unit, especially on the front side of a display and operating unit of the transfer unit. A counter-patient inhalation port is preferably an inspiratory tube port for connection to the patient inhalation port, i.e., the inspiratory patient port of the transfer unit. A patient exhalation port is especially an expiratory patient port of the transfer unit, especially on the front side of a display and operating unit of the transfer unit. A counter-patient exhalation port is preferably an expiratory tube port for connection to the patient exhalation port, i.e., the expiratory patient port of the transfer unit. A ventilation exhalation port is preferably an expiratory gas outlet at the transfer unit, especially on the rear side of the transfer unit. A counter-ventilation exhalation port is correspondingly preferably an expiratory gas inlet into the ventilation unit. A ventilation inhalation port is preferably an inspiratory gas inlet at the transfer unit, especially on the rear side of the nonreturn device, while a counter-ventilation inhalation port is preferably an inspiratory gas outlet from the ventilation unit.

A breathing air section is especially a line element for guiding expiratory breathing gases, i.e., for guiding exhaled gases. An exhaled air section is especially a line element for guiding inspiratory breathing gases, i.e., for guiding inhaled gases.

A transfer unit according to the present invention is provided, together with a ventilation unit, to form a ventilator for carrying out a ventilation process of a patient. The transfer unit has for this purpose both a breathing air section and an exhaled air section. A breathing air can be guided through the breathing air section for the ventilation of the patient from a ventilation inhalation port, which is configured for a fluid-communicating connection to a corresponding counter-ventilation inhalation port of the ventilation unit in the interior of the transfer unit, to a patient inhalation port, and a counter-patient inhalation port of a ventilation tube element may, in turn, be mounted at the patient inhalation port. The exhaled air section has a corresponding configuration as well. Thus, the exhaled air section also has a ventilation exhalation port, which is configured for a fluid-communicating connection at the ventilation unit, especially at a counter-ventilation exhalation port of the ventilation unit. A connection, especially a fluid-communicating connection, to a counter-patient exhalation port of the ventilation tube element may be provided by a patient exhalation port. The ventilation tube element may then be used, in turn, to feed the breathing air and the exhaled air to the patient and to discharge same away from the patient. In other words, a breathing air can be sent through the breathing air section and the exhaled air section through the transfer unit such that a breathing air flows to the patient and an exhaled air comes from the patient. To ensure a secure mounting of the transfer unit at the ventilation unit to form the ventilation device, the transfer unit according to the present invention further has a mounting section. The transfer unit can be mounted especially reversibly at a corresponding counter-mounting section of the ventilation unit via this mounting section. In other words, the transfer unit may be mounted at the ventilation unit and can be removed from same. In particular, the transfer unit can be transferred between different ventilation units, which have a corresponding counter-mounting section each.

Provisions are made in a transfer unit according to the present invention for a breathing valve with a first nonreturn device to be mounted in the breathing air section. A nonreturn device in the sense of the present invention may be configured especially as a nonreturn valve. In the sense of the present invention, a nonreturn device makes possible, in particular, a flow of a fluid in one direction, while a flow of the fluid in the opposite direction is blocked by the nonreturn device. This nonreturn device is mounted in the breathing air section such that a flow of breathing air can be ensured, and this flow has a breath flow direction that points from the ventilation inhalation port to the patient inhalation port. In other words, the breathing air can be guided through the transfer unit, especially coming from the ventilation unit, and passed on to the ventilation tube element and thus ultimately to the patient. It can be ensured by the provision of a nonreturn device, in particular, that a flow of the breathing air in the opposite direction, i.e., arriving from the patient in the direction of the ventilation unit, can be prevented from occurring. In particular, exhalation via this breathing air section can be prevented in this manner.

This has especially the advantage that an exhalation process of the patient is carried out at least essentially exclusively via the exhaled air section of the transfer unit according to the present invention. An exhalation valve with a second nonreturn device is mounted according to the present invention in this exhaled air section. This second nonreturn device ensures again, in particular, a flow of exhaled air with an exhalation flow direction, and this exhalation flow direction now points from the patient exhalation port to the ventilation exhalation port. It can be ensured by the second nonreturn device here as well that an opposite flow of the exhaled air, i.e., from the ventilation unit to the patient, can be ruled out.

As an essential feature of the present invention, the exhalation valve has, in addition to the second nonreturn device, a minimum pressure device. This minimum pressure device is configured especially such that it can ensure a minimum pressure of the exhaled air. In other words, a flow of exhaled air in the exhalation flow direction from the patient exhalation port to the ventilation exhalation port is only released when the exhaled air has a pressure that exceeds this minimum pressure. In case of an exhaled air of the patient that is lower than the minimum pressure, the minimum pressure device closes the exhalation valve, so that it can be ensured hereby, in particular, that a minimum pressure of air will remain in the lungs of the patient. In other words, a positive end-expiratory pressure (PEEP) can be secured and preferably also set for a patient by this minimum pressure device.

In summary, it can be made possible by a transfer unit according to the present invention that a ventilator used for a ventilation process of a patient can be changed by transferring the transfer unit from a first ventilation unit of a first ventilator to a second ventilation unit of a second ventilator. It can be made possible by a transfer unit according to the present invention, in particular, during this transfer of the ventilation process from one ventilator to another ventilator that, on the one hand, a breathing process of the patient is not blocked completely, and, on the other hand, it can, moreover, be ensured, in particular, that a certain minimum pressure of breathing air (PEEP) will always remain in the lungs of the patient.

Further, a transfer unit according to the present invention can be perfected such that the transfer unit has a data unit with a data interface for a data-communicating connection to a counter-data interface of the ventilation unit and has a memory element connected to the data interface in a data-communicating manner for the storage of data, especially at least one ventilation parameter of the ventilation process and/or at least one measured variable and/or target variable indicating the ventilation process and/or the ventilation parameter, at least from time to time. It can be made possible by such a data unit, especially by a memory element of the data unit, that information, especially information on the ventilation process of the patient, which is being currently performed, can be stored in the transfer unit. A transfer of the data, for example, from a higher-level control unit of the ventilator or ventilation system or directly from the ventilation unit that is currently becoming active, to the transfer unit can be made possible via a data interface, which can be connected to a counter-data interface of the ventilation unit in a data-communicating manner. This data-communicating connection may be a wired and/or wireless connection, for example, via a plug-type connection, WLAN, Bluetooth, infrared or the like. It can be made possible in this manner, for example, that not only can the ventilation process of the patient be transferred from one ventilation unit to a second ventilation unit, but also that after mounting the transfer unit at the new ventilation unit, the data being stored in the memory element, for example, especially data of ventilation parameters of the ventilation process and/or of at least one measured variable or target variable indicating the ventilation process and/or the ventilation parameter, can be additionally transferred to this transfer unit. An especially good, continuous and/or interruption-free continuation of the ventilation process of the patient, especially while maintaining the corresponding ventilation parameters, can be made possible in this manner.

A transfer unit according to the present invention can also be perfected such that the data unit has at least one sensor element for determining measured data of the ventilation process at least from time to time and especially a computer (comprising one or more processors and/or one or more processors and associated memory) for analyzing the measured data of the at least one sensor element, the measured data and/or the analysis results being preferably able to be stored in the memory element. It can be made possible by such a sensor element directly in the transfer unit that the ventilation information of the patient, which arises during the transfer process, can also be determined especially during the transfer process, preferably analyzed by the unit, and then preferably stored in the memory element. A continuous and/or interruption-free monitoring of the ventilation process of the patient, especially also during the transfer of the transfer unit from one ventilation unit to the next, can be made possible and/or ensured in this manner.

A transfer unit according to the present invention may also be perfected such that the data unit has a display element for displaying at least data stored in the memory element at least from time to time. Such a display element may be, for example, a display screen element for a visual display, but also a loudspeaker element as well as configured for an acoustic display of the stored data. It can be made possible in this manner to provide the stored data and/or information especially fast and in a reliable manner.

According to a variant, provisions may be made in a transfer unit according to the present invention for the data unit to have at least one input element for setting the data unit, especially for setting the data stored in the memory element and/or the at least one sensor element and/or the computer and/or the display element, the operating element preferably being integrated in the at least one display element. Provisions can be made, in particular, by such an input element for improving the operatability of the transfer unit. The input element may be configured, for example, as a switch, a rotary and/or sliding control, keyboard or the like. Data, which shall be stored in the memory element, can be entered directly, and monitoring areas can be defined for the sensor element, instructions can be sent to a computer and/or settings of the display element can be carried out by the input element. The operating element may especially preferably also be integrated in the display element, for example, as a touch-sensitive touchscreen.

A transfer unit according to the present invention may also be configured such that the transfer unit, especially the mounting section, has a locking device with a locking element for reversibly and controllably fixing the transfer unit at the ventilation unit. The ventilation process of the patient requires essentially that a ventilator be present, which comprises a transfer unit, which is mounted at a ventilation unit. An unintended removal of the transfer unit from the ventilation unit may cause in the worst case the ventilation process of the patient to be interrupted. Due to a locking device, which is preferably mounted at the mounting section, it can be ensured by the existing locking element of the locking device that the transfer unit is fixed at the ventilation unit and it also remains fixed there. A simple, especially unintended, pulling off or removal of the transfer unit from the ventilation unit can be avoided or prevented by such a locking device with a locking element.

A transfer unit according to the present invention may preferably be perfected such that the locking device has an operating element for establishing and/or releasing the fixation of the transfer unit at the ventilation unit, the operating element preferably being integrated in the input element of the data unit. It can be made possible by such an operating element, for example, a push switch, that release of the fixation of the transfer unit at the ventilation unit only takes place when the corresponding operating element of the locking device has explicitly been activated, for example, by a user. An unintended opening of the locking device and hence of the locking element of the locking device can be made more difficult in this manner.

A transfer unit according to the present invention can especially preferably be perfected such that the locking element is configured as a mechanical and/or electromechanical and/or magnetic and/or pneumatic and/or hydraulic locking element. Especially a non-positive and/or positive-locking fixation of the transfer unit at the respective ventilation unit can be provided, especially in a controllable manner, by the locking element in each of these different embodiments of the locking element. Depending on the location of use and the configuration, the broadest possible range can be made possible in terms of the construction and design of the locking element of the transfer unit according to the present invention by the different possible embodiments of the locking element.

A transfer unit according to the present invention may also be configured such that the transfer unit has an energy unit with a preferably chargeable energy storage element for supplying the transfer unit with electrical energy. It is advantageous, especially if a transfer unit according to the present invention has electrical and/or electronic components, for example, a display element, a storage element and/or a computer, to provide electrical energy by an energy unit with an energy storage element. The energy storage element may be configured, for example, as a battery, rechargeable battery and/or capacitor. Operation of the electrical and/or electronic components can also be made possible and especially ensured in this manner during a transfer of the transfer unit from one ventilation unit to the next.

According to a variant of a transfer unit according to the present invention, provisions may, furthermore, be made for the energy unit to have an energy interface connected in an energy-communicating manner to the energy storage element for the energy-communicating connection to a counter-energy interface of the ventilation unit for a preferably repeated charging of the energy storage element with electrical energy. Provisions may especially preferably be made for this energy storage element to be able to be charged, especially repeatedly, for which it is connected to an energy interface of the transfer unit in an energy-communicating manner. This energy interface is configured, in turn, with a counter-energy interface of the ventilation unit for the energy-communicating connection. The energy storage element can be charged in this manner at a transfer unit that is mounted at a ventilation unit and electrical energy can be made available in this manner for the next transfer of the transfer unit from one ventilation unit to the next. The energy interface represents especially a port for energy supply for the transfer unit. The counter-energy interface represents especially a port for providing energy and for supplying energy for the ventilation unit.

Furthermore, provisions may be made in a transfer unit according to the present invention for the minimum pressure device to have a pressure-controlled and/or electromechanical and/or mechanical setting element for setting the minimum pressure in the exhaled air section. As was described above, it can be ensured by the minimum pressure device that a residual pressure remains in the lungs of the patient after an exhalation process. This minimum pressure can now be set in the exhaled air section by a setting element and adapted especially fittingly to the patient-specific ventilation process of the patient in question. An individually adapted positive end-expiratory pressure can be set in this manner by a transfer unit according to the present invention for each patient being ventilated and it can also be maintained during a transfer of the transfer unit from one ventilation unit to the next.

According to a second aspect of the present invention, the object is accomplished by a ventilator for carrying out a ventilation process of a patient, having a ventilation unit with a pneumatic unit for carrying out the ventilation process, a transfer unit mounted reversibly at the ventilation unit as well as a control unit for the controlled operation of the pneumatic unit, wherein a mounting section of the transfer unit is mounted reversibly at a counter-mounting section of the ventilation unit, wherein a ventilation inhalation port of the transfer unit is further connected in a fluid-communicating manner to a counter-ventilation inhalation port of the ventilation unit, wherein a ventilation exhalation port of the transfer unit is further connected in a fluid-communicating manner to a counter-ventilation exhalation port of the ventilation unit. A ventilator according to the present invention is characterized in that the transfer unit is configured according to the first aspect of the present invention. All the advantages that have been described in detail with reference to a transfer unit according to the first aspect of the present invention may thus also be provided by a ventilator according to the second aspect of the present invention, which has such a transfer unit according to the first aspect of the present invention.

In addition to the transfer unit according to the present invention, a ventilator according to the present invention also has a ventilation unit. To form the ventilator, the transfer unit is mounted reversibly at the ventilation unit, especially the mounting section of the transfer unit at the counter-mounting section of the ventilation unit. The ventilation process of the patient proper is provided at least essentially by the ventilation unit, especially the pneumatic unit of the ventilation unit. A control unit of the ventilator ensures that the ventilation process is carried out according to the pre-defined ventilation parameters and/or ventilation target variables. A ventilator according to the present invention may be configured such that the ventilation unit is configured as a stationary and/or as a mobile ventilation unit. A stationary ventilation unit in the sense of the present invention may be especially a ventilation unit that is connected to a central, stationary ventilation system which is thus especially installed permanently in a building. A mobile ventilation unit may, by contrast, be, for example, a ventilation unit, which is, for example, movable with a hospital bed and/or is mounted in a vehicle for transporting the patient being ventilated. An especially high level of mobility of the patient being ventilated can be made possible in this manner.

Furthermore, provisions may be made in a ventilator according to the present invention for the control unit to be integrated in the transfer unit and/or the ventilation unit. In other words, the control unit may be integrated in the ventilation unit, as a result of which the control of the pneumatic unit is carried out by the respective ventilation unit especially in case of ventilation units having the same configuration. In this case, the transfer unit has at least essentially the function or task of providing the ventilation process for the patient during the transfer of the transfer unit between the ventilation units such that at least a positive end-expiratory pressure continues to be maintained. As an alternative or in addition, the control unit may also be integrated in the transfer unit, as a result of which the transfer unit itself is used for the control proper of the pneumatic units of the ventilation units of the ventilators and thus of the entire ventilation process. Provisions may be made in this manner for an especially continuous continuation of the ventilation process to be able to be made possible.

Moreover, provisions may be made in a ventilator according to the present invention for a data interface of the transfer unit to be connected in a data-communicating manner to a counter-data interface of the ventilation unit and/or for an energy interface of the transfer unit to be connected to a counter-energy interface of the ventilation unit in an energy-communicating manner. Transmission of data between the transfer unit and the ventilation unit, on the one hand, can be made possible in this manner. In particular, a transmission of ventilation parameters and/or of ventilation target variables indicating the ventilation process can thus also be made possible during a transfer of the transfer unit between different ventilators. As an alternative or in addition, electrical energy can also be transmitted between the transfer unit and the ventilation unit. Charging of an electrical energy storage device of the transfer unit for providing electrical energy for electrical and/or electronic components of the transfer unit can be made possible hereby.

Moreover, provisions may be made in a ventilator according to the present invention for the ventilation unit and/or the transfer unit to have at least one of the following elements:
a locking device for the reversible and controllable fixation of the transfer unit at the ventilation unit, especially having an operating element,
a display element for the display of data, especially data of the ventilation process, at least from time to time, and/or
an input element for setting the transfer unit and/or the ventilation unit.

This list is not complete, so that the ventilation unit and/or the transfer unit may also have additional elements. It can be ensured by the locking device, in particular, that an unintended removal of the transfer unit from the ventilation unit can be prevented. In turn, information on the ventilation process and/or on the state of the entire ventilator can be displayed by a display element. Parameters of the ventilation process can be varied and/or, for example, an imminent transfer of a transfer unit from one ventilation unit to the other to a next ventilation unit can be initiated by an input element.

According to a third aspect of the present invention, the object is accomplished by a ventilation system for carrying out a ventilation process of a patient, comprising a transfer unit according to the first aspect of the present invention and at least two ventilation units, the at least two ventilation units having each at least one pneumatic unit for carrying out the ventilation process, a counter-mounting section for the reversible mounting of a mounting section of the transfer unit, a counter-ventilation inhalation section for fluid-communicating connection in a ventilation inhalation port of the transfer unit, as well as a counter-ventilation exhalation port for fluid-communicating connection to a ventilation exhalation port of the transfer unit. A ventilation system according to the present invention is characterized in that the transfer unit can be mounted reversibly at each of the at least two ventilation units to form a ventilator according to the second aspect of the present invention.

A ventilation process of a patient can be carried out by a ventilation system according to the present invention. The ventilation system according to the present invention has, in particular, especially a transfer unit according to the first aspect of the present invention. All the advantages that have been described in detail in reference to a transfer unit according to the first aspect of the present invention can thus also be provided by a ventilation system according to the present invention according to the third aspect of the present invention. Moreover, a ventilation system according to the present invention has at least two ventilation units. These ventilation units are identical at least in terms of essential components in that the transfer unit according to the first aspect of the present invention can be mounted on both ventilation units. Thus, both ventilation units have a pneumatic unit in order to make it possible to carry out a ventilation process of the patient. Further, both ventilation units have a counter-mounting section each for a reversible mounting of the mounting section of the transfer unit. A counter-ventilation inhalation port as well as a counter-ventilation exhalation port are correspondingly present at the ventilation units in order to make it possible to connect the ventilation inhalation port and correspondingly the ventilation exhalation port of the transfer unit in a fluid-communicating manner. It can be ensured in this manner that the ventilation process can be carried out by both ventilation units in cooperation with the transfer unit according to the present invention according to the first aspect of the present invention. It is thus possible to provide especially the feature according to the present invention of a ventilation system according to the present invention, namely, that the transfer unit can be mounted reversibly at each of the at least two ventilation units to form a ventilator according to the second aspect of the present invention. All the advantages that were already described in detail in reference to a ventilator according to the present invention according to the second aspect of the present invention can also be provided in this manner in a ventilation system according to the present invention according to the third aspect of the present invention.

According to a fourth aspect of the present invention, the object is accomplished by a process for changing a ventilator used for a ventilation process of a patient in a ventilation system according to the fourth aspect of the present invention, wherein a ventilation system includes the transfer unit that can be mounted at a first ventilation unit to form a first ventilator and at a second ventilation unit to form a second ventilator, and wherein the ventilation process is carried out at the beginning of the process by the first ventilator. A process according to the present invention is characterized by the following steps:

a) Transfer of the second ventilation unit into a receiving mode,
b) removal of the transfer unit from the first ventilation unit, wherein the removal comprises an activation of the breathing valve and of the exhalation valve of the transfer unit,
c) mounting of the transfer unit at the second ventilation unit to form the second ventilator, and
d) ending the receiving mode of the second ventilation unit as well as starting of the ventilation process by the second ventilator.

A process according to the present invention according to the fourth aspect of the present invention is carried out by a ventilation system according to the present invention according to the third aspect of the present invention. Such a ventilation system according to the third aspect of the present invention has especially a transfer unit according to the first aspect of the present invention as well as two or more ventilators according to the second aspect of the present invention. All the advantages that have been described in reference to a transfer unit according to the first aspect of the present invention, in reference to a ventilator according to the second aspect of the present invention as well as in reference to a ventilation system according to the third aspect of the present invention can thus also be provided by a process for changing the ventilator used for a ventilation process of a patient in a ventilation system according to the fourth aspect of the present invention.

A change of a ventilator being used can be provided for a ventilation process of a patient by a process according to the present invention. A ventilator in the sense of the present invention comprises especially a transfer unit, which is mounted at a ventilation unit. At the beginning of the process, the transfer unit is mounted at a first ventilation unit and forms the first ventilator there for carrying out the ventilation process of the patient. The ventilation process shall now be transferred by a process according to the present invention to a second ventilator, and this is carried out especially by a transfer of the transfer unit from the first ventilation unit to the second ventilation unit. Provisions may be made, in particular, for one of the two ventilators to be configured as a stationary ventilator and for the other to be configured as a mobile ventilator.

To carry out the change of the ventilators, the second ventilation unit is put into a receiving mode in a first step a) of a process according to the present invention. In the sense of the present invention, this means especially that the second ventilation unit is prepared for a planned and especially subsequent mounting of the transfer unit with its mounting section at the counter-mounting section of the second ventilation unit, for example, by a corresponding actuation of the counter-ventilation port or the counter-ventilation exhalation port of the second ventilation unit.

The transfer unit is removed from the first ventilation unit in the next step b). The breathing valve and the exhalation valve of the transfer unit are activated, especially automatically, during this removal. In other words, the patient can perform an inhalation process, preferably independently, via the breathing valve after the removal of the transfer unit. The exhalation valve makes, in turn, possible an exhalation process of the patient via the second nonreturn device, and a positive end-expiratory pressure is ensured for this exhalation process of the patient especially by the minimum pressure device of the exhalation valve.

The next step c) of a process according to the present invention already comprises especially the mounting of the transfer unit at the second ventilation unit, as a result of which the second ventilator is formed via the connection of the transfer unit to the second ventilation unit. The mounting of the transfer unit also comprises especially the fluid-communicating connection of the ventilation inhalation port of the transfer unit to the counter-ventilation inhalation port of the second ventilation unit as well as correspondingly the fluid-communicating connection of the ventilation exhalation port of the transfer unit at the counter-ventilation exhalation port of the second ventilation unit. In other words, the second ventilator is configured and prepared for providing a ventilation process for the patient after mounting the transfer unit on the second ventilation unit.

In the last step d), a process according to the present invention is continued, and, in particular, the receiving mode of the second ventilation unit, which was set in step a) of a process according to the present invention, is ended, and the ventilation process is started by the second ventilator. This starting of the ventilation process comprises especially an actuation of the pneumatic unit of the second ventilation unit by the control unit of the ventilator. After the end of step d) of a process according to the present invention, the ventilation process is thus transferred from the first ventilator to the second ventilator. It was made possible by the use of a transfer unit according to the first aspect of the present invention to at least maintain or continuously provide a positive end-expiratory pressure during this transfer. If the ventilator is, for example, a mobile ventilator, transportation of the entire patient being ventilated can now be carried out.

A process according to the present invention can be perfected such that the first ventilation unit is put into the receiving mode in step b) after removal of the transfer unit from the first ventilation unit, and the receiving mode of the first ventilation unit is ended especially in step d). As was described above, a receiving mode of a ventilation unit is, in the sense of the present invention, especially a mode of the ventilation unit in which the corresponding ventilation unit is prepared for the mounting of the transfer unit. By putting the first ventilation unit into this receiving mode after removal of the transfer unit, provision can especially advantageously be made for mounting the transfer unit again at the first ventilation unit simply, rapidly and reliably to form again the first ventilator if mounting the transfer unit at the second ventilation unit is prevented especially for unforeseeable reasons. Resumption or continuation of the ventilation process by the first ventilator can thus be made possible in this manner in an especially simple manner. A needlessly long duration of the transfer process or even a complete interruption of the ventilation process of the patient can be prevented in this manner.

Further, provisions may also be made in a process according to the present invention for carrying out at least one of the following processes before step b):

Transmission of data, especially at least one ventilation parameter of the ventilation process and/or of at least one measured variable and/or target variable indicating the ventilation process and/or the ventilation parameter from the first ventilation unit to a storage element of the transfer unit, charging of an energy storage element of the transfer unit, and actuation of a setting element of a minimum pressure device of an exhalation valve to the transfer unit to set a minimum pressure in the exhaled air section.

A process according to the present invention can be further improved in this manner. For example, data on the ventilation process can thus be transmitted to the transfer unit, especially to a storage element of the transfer unit. Transmission of these data to the second ventilation unit and in this manner an at least essentially continuous ventilation process, which is not influenced by the change of the ventilator or is influenced only insignificantly, can thus be made possible. The transfer process of the transfer unit from one ventilation unit to the next ventilation unit can also be improved by the charging of an energy storage element, because electrical energy can be provided especially by the energy storage element for the functionalities of electrical and/or electronic elements of the transfer unit, especially during the performance proper of the transfer of the transfer unit. The actuation of a setting element of a minimum pressure device of the exhalation valve of the transfer unit makes possible especially a preferably patient-adapted setting of a minimum pressure in the exhaled air section. It can be made possible in this manner, in particular, that a positive end-expiratory pressure, which is an important ventilation parameter of a ventilation process of the patient, can be provided as a constant or at least essentially constant pressure during the transfer process of the transfer unit between the ventilation units and also subsequently during the performance of the ventilation process by the second ventilator.

A process according to the present invention may especially preferably be perfected such that data stored in the memory unit are transferred at least partially to the second ventilation unit in step c) and/or d) after mounting the transfer unit at the second ventilation unit. As was described above, data on the ventilation process, which was carried out by the first ventilator, may be stored in the memory element. These data may comprise especially ventilation parameters and/or ventilation target variables indicating the ventilation process. It can be ensured by a transmission of these stored data at least partially from the transfer unit to the second ventilation unit, with which together the transfer unit forms the second ventilator after the transfer of the transfer unit, that these stored data of the ventilation process are available to the second ventilator. An especially continuous ventilation process, especially in respect to the stored ventilation parameters and/or ventilation target variables, can be ensured in this manner.

A process according to the present invention may especially preferably be perfected such that feasibility of the change of the ventilator is checked before step b), especially before step a), and if the result of the checking is negative, removal of the transfer unit from the first ventilation unit is prevented by blocking the locking device. It can especially be ensured by this checking that a removal of the transfer unit cannot be carried out at all in cases in which, for example, mounting of the transfer unit at the second ventilation unit is prevented. This may preferably be brought about, for example, by blocking the locking device. The transfer unit remains in this case at the first ventilation unit and the ventilation process is thus continued by the first ventilator without interruption. The security for the patient being ventilated can be increased hereby.

Further actions improving the present invention appear from the following description of exemplary embodiments of the present invention, which are shown in the figures. All the features and/or advantages appearing from the claims, from the description and from the drawings, including design details and arrangements in space, may be essential for the present invention both in themselves and in the different combinations. Elements having the same function and mode of action are provided with the same reference numbers in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
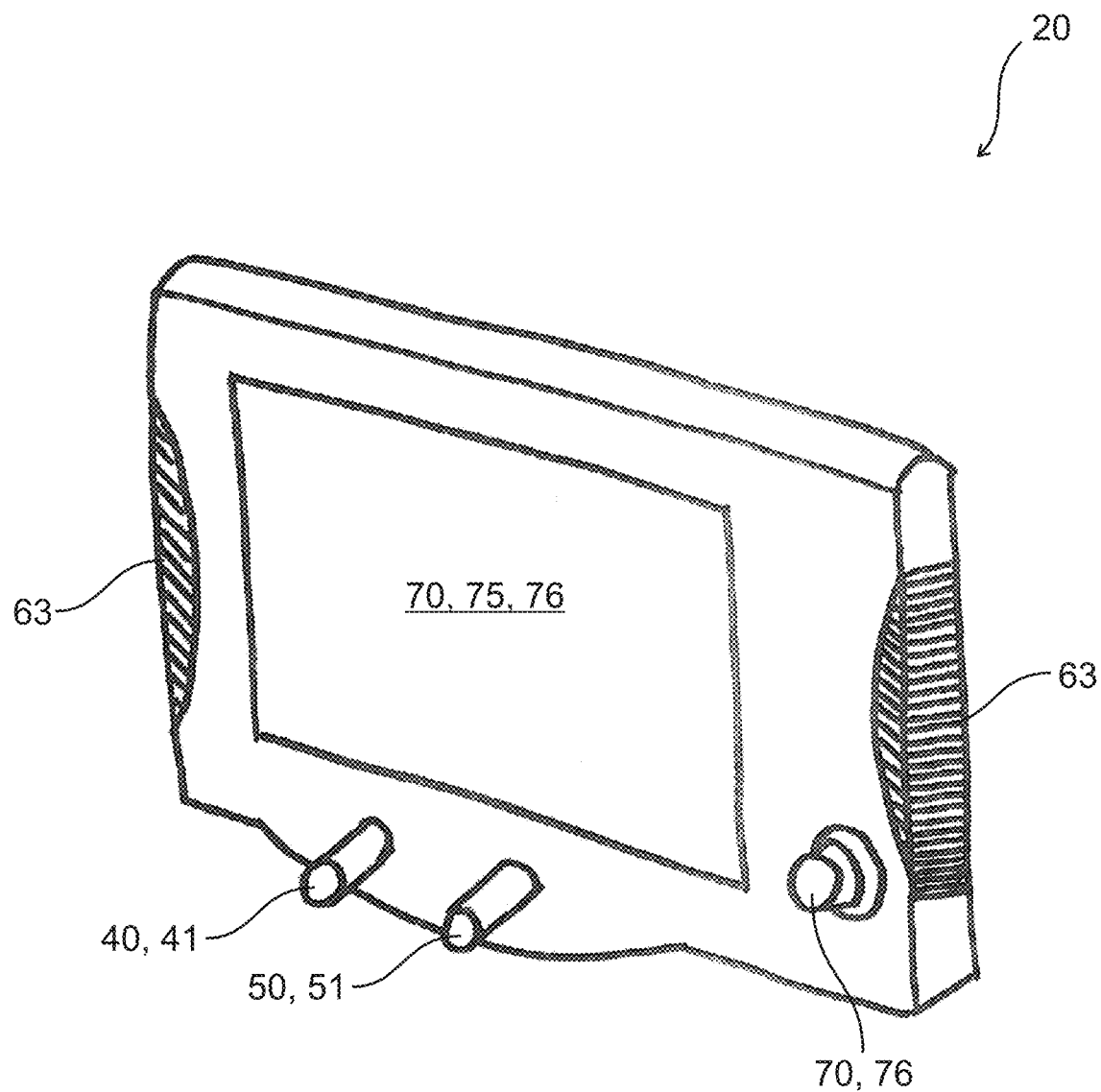
FIG. 1 is a front view of a transfer unit according to the present invention.
Figure 2:
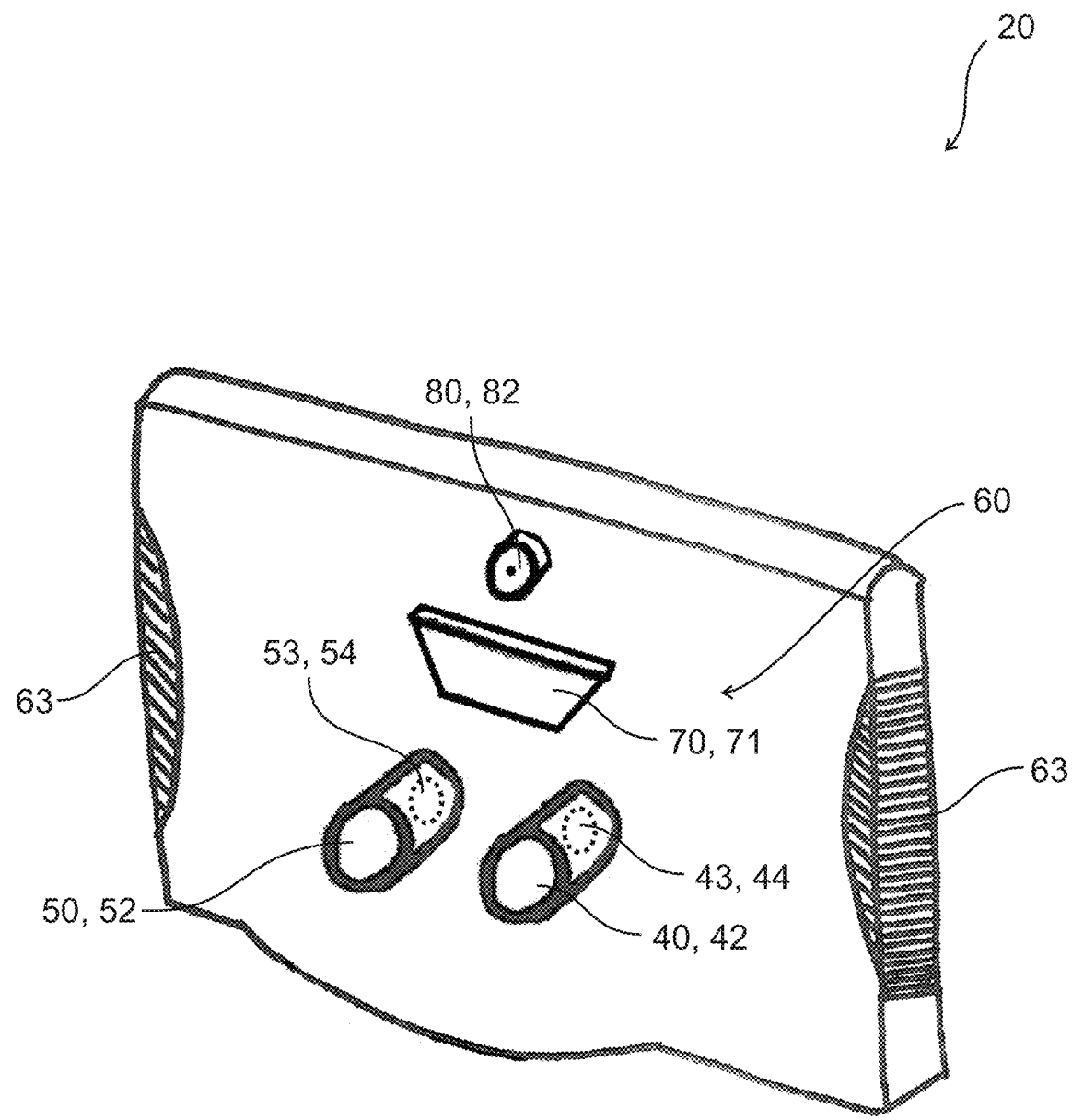
FIG. 2 is a rear view of a transfer unit according to the present invention.
Figure 3:
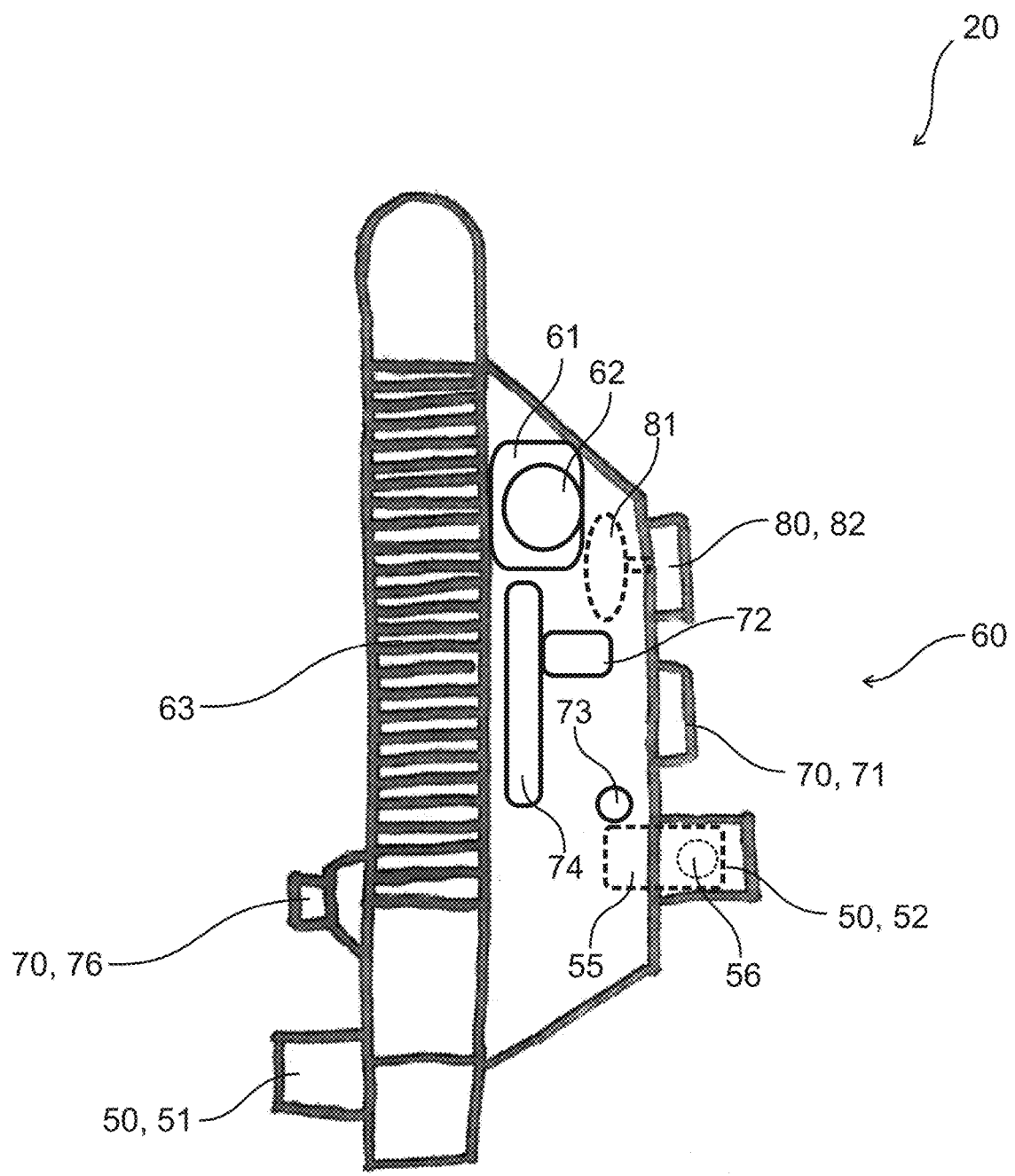
FIG. 3 is a lateral view of a transfer unit according to the present invention, schematically showing some internal features.

Referring to the drawings, FIGS. 1 through 3 show a possible embodiment of a transfer unit 20 according to the present invention in different views. Thus, FIG. 1 shows a front view, FIG. 2 shows a rear view and FIG. 3 shows a lateral view of the transfer unit 20 according to the present invention. FIGS. 1 through 3 will therefore be described below together, and the details will always be discussed separately.

A transfer unit 20 according to the present invention is intended especially for being mounted on a ventilation unit 10 to form a ventilator 1 (neither of which is shown). It has for this purpose especially the mounting section 60 shown in FIGS. 2 and 3. The mounting section 60 comprises especially a locking device 61 with a locking element 62, see FIG. 3, as a result of which fixation of the transfer unit 20 at a ventilation unit 10 can be made possible. The locking elements 62 may have, for example, a mechanical, electromechanical, magnetic, pneumatic and/or hydraulic configuration. Operating elements 63 make it possible to set this fixation, especially a releasing of the locking element 62 elicited by a user. Further, especially a ventilation exhalation port 52 of an exhaled air section 50 as well as a ventilation inhalation port 42 of a breathing air section 40 of the transfer unit 20 are mounted at the mounting section 60. The ventilation exhalation port 52 as well as the ventilation inhalation port 42 are configured each for a fluid-communicating connection with a corresponding counter-ventilation inhalation port 11 and counter-ventilation exhalation port 12 of the ventilation unit 10 (see FIG. 4). A breathing valve 43, which has especially a first nonreturn device 44, is mounted in the breathing air port 40. It can be made possible in this manner that a breathing air 90 can be ensured with a breathing air flow 91 (not shown) from the ventilation inhalation port 42 to the patient inhalation port 41 (see FIG. 1). Analogously to this, the exhaled air section 50 in the ventilation exhalation port 52 has an exhalation valve 53, which likewise has especially a second nonreturn device 54, see especially FIG. 2. It can be ensured by this exhalation valve 53 especially that an exhalation flow direction 93 of the exhaled air 92 (not shown) points always and at any time from the patient exhalation port 51 shown in FIG. 1 to the ventilation exhalation port 52. Moreover, and according to the present invention, a minimum pressure device 55 is mounted, as is shown in FIG. 3, in the exhaled air section 50. It can be ensured by this minimum pressure device 55, in particular, that the exhaled air 92 of the patient will have a pressure not lower than a certain minimum pressure. It can be ensured, in particular, by a setting element 56 that this ensured minimum pressure can be set in a patient-adapted manner. In other words, a positive end-expiratory pressure (PEEP), which can be set individually for the patient and which can also be provided by the transfer unit 20 according to the present invention independently from a ventilator 1 (not shown), for example, in case of a change of the ventilator 1, can thus be set by a transfer unit 20 according to the present invention. Another component of a transfer unit 20 according to the present invention may be a data unit 70. This data unit 70 has especially a data interface 71, which is configured for a data-communicating connection to a counter-data interface 14 of the ventilation unit 10 (neither of which is shown). The data interface 71 may, in turn, be connected in a data-communicating manner in the transfer unit 20, for example, with a computer 74, with a memory element 72 or also with a sensor element 73. For example, the ventilation process can be monitored by such a sensor element 73. The computer 74 may preferably be configured for analyzing the data determined by the sensor element 73. The memory element 72 makes it, in turn, possible to store data, which are generated, for example, by the transfer unit 20 itself, and also to transfer data, for example, prior to a performed transfer of the transfer unit 20 via the data interface 71. A wired data interface 71 is shown, and wired data interfaces 71 may also be provided according to the present invention. The data, which are stored especially in the memory element 72, may especially also be displayed via a display element 75 of the data unit 70. A change or an actuation of the computer 74, of the sensor element 73 and of additional elements of the data unit 70 can be carried out via an input element 76, which may also be integrated, for example, in the display element 75. To supply especially the data unit 70 with electrical energy, a transfer unit 20 according to the present invention may further have an energy unit 80 with especially one energy storage element 81. This energy storage element 81 may preferably be charged reversibly via an energy interface 82, which is configured for an energy-communicating connection to a counter-energy interface 15 of a ventilation unit 10 (not shown). Reliable operation by electrical energy provided by the energy storage element 81 can be ensured in this manner especially during a transfer of the transfer unit 20 from one ventilation unit 10 to another ventilation unit 10.

Figure 4:
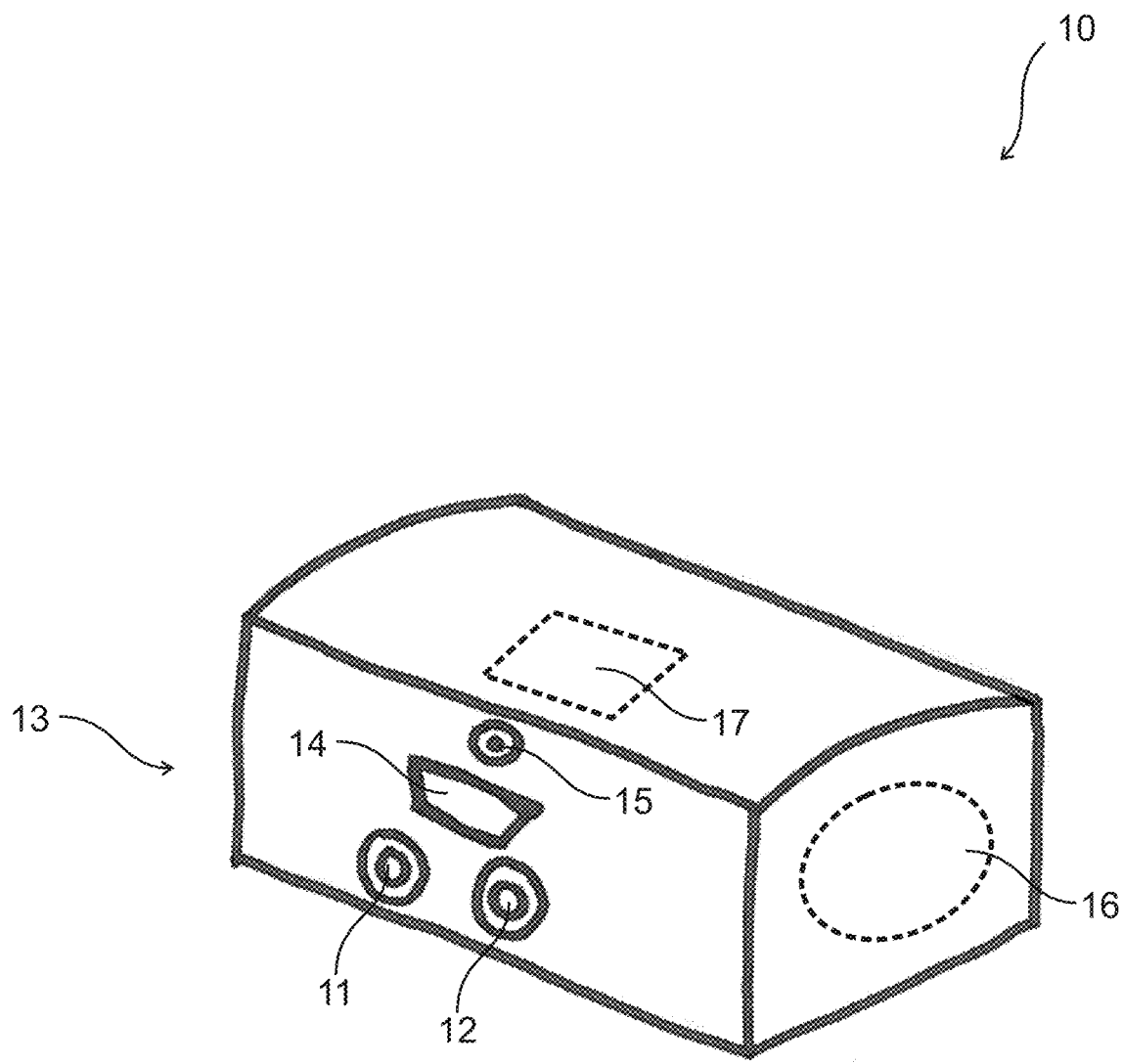
FIG. 4 is a perspective view of an embodiment of a ventilation unit.

FIG. 4 shows a ventilation unit 10, as it can form a ventilator 1 according to the present invention together with a transfer unit 20 according to the present invention (neither of which is shown). For a reliable response of the needed transfer unit 20, the ventilation unit 10 has a counter-mounting section 13. This counter-mounting section 13 is configured especially with interfaces in order to correspond to the corresponding interfaces of the transfer unit 20. Thus, the counter-mounting section 13 has especially a counter-ventilation inhalation port 11 as well as a counter-ventilation exhalation port 12 for respective fluid-communicating connections to a ventilation inhalation port 42 and correspondingly to a ventilation exhalation port 52 (neither of which is shown) of the transfer unit 20. A data interface 71 of a ventilation unit 10 (neither of which is shown) can be connected in a data-communicating manner via a counter-data interface 14. An energy interface 82 of a transfer unit 20 (neither of which is shown) for charging an energy storage element 81 of the transfer unit 20 can correspondingly be used via a counter-energy interface 15. To provide the ventilation process of the patient, the ventilation unit 10 has especially a pneumatic unit 16. In this embodiment of the ventilation unit 10, the latter has, furthermore, a control unit 17 for actuating this pneumatic unit 16. As an alternative or in addition, this control unit 17 may also be integrated into a transfer unit 20 (not shown).

Figure 5:
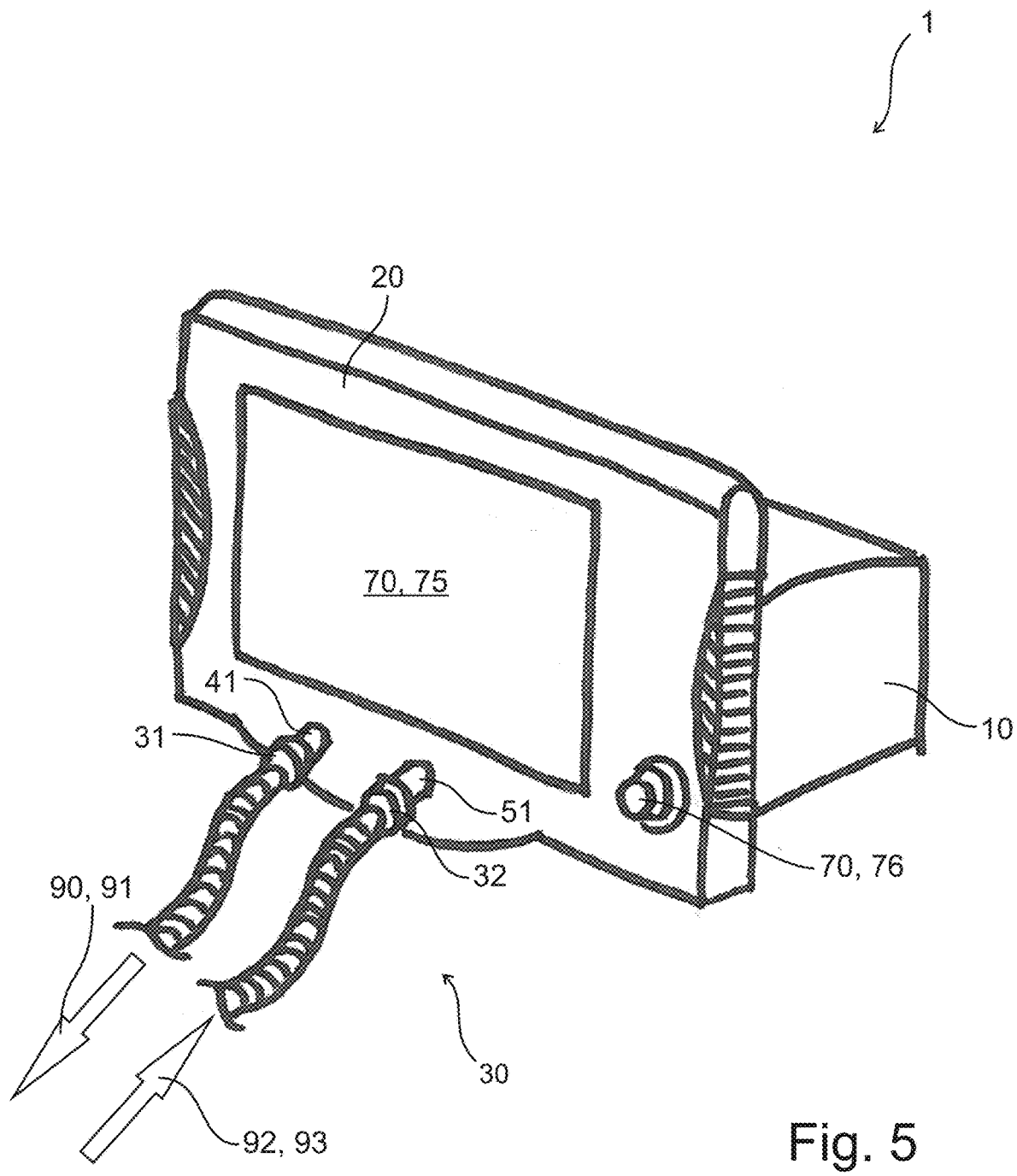
FIG. 5 is a perspective view of a first embodiment of a ventilator according to the present invention.

FIG. 5 shows a possible embodiment of a ventilator 1 according to the present invention. In particular, a transfer unit 20 is mounted at a ventilation unit 10. Reference is made to FIGS. 1 through 3 as well as to FIG. 4 for possible embodiments of the ventilation unit 10 as well as of the transfer unit 20. Further, a ventilation tube element 30 is already mounted at the patient inhalation port 41 or at the patient exhalation port 51 of the transfer unit 20 in this embodiment shown. The ventilation tube element 30 has for this purpose especially a counter-patient inhalation port 31 as well as a counter-patient exhalation port 32. Breathing air 90 with a breathing air flow direction 91 as well as exhaled air 92 with an exhaled air flow direction 93 are also shown for better understanding. Further, a display element 75 of a data unit 70 as well as an input element 76 of the data unit 70 are shown in this embodiment as a part of the transfer unit 20.

Figure 6:
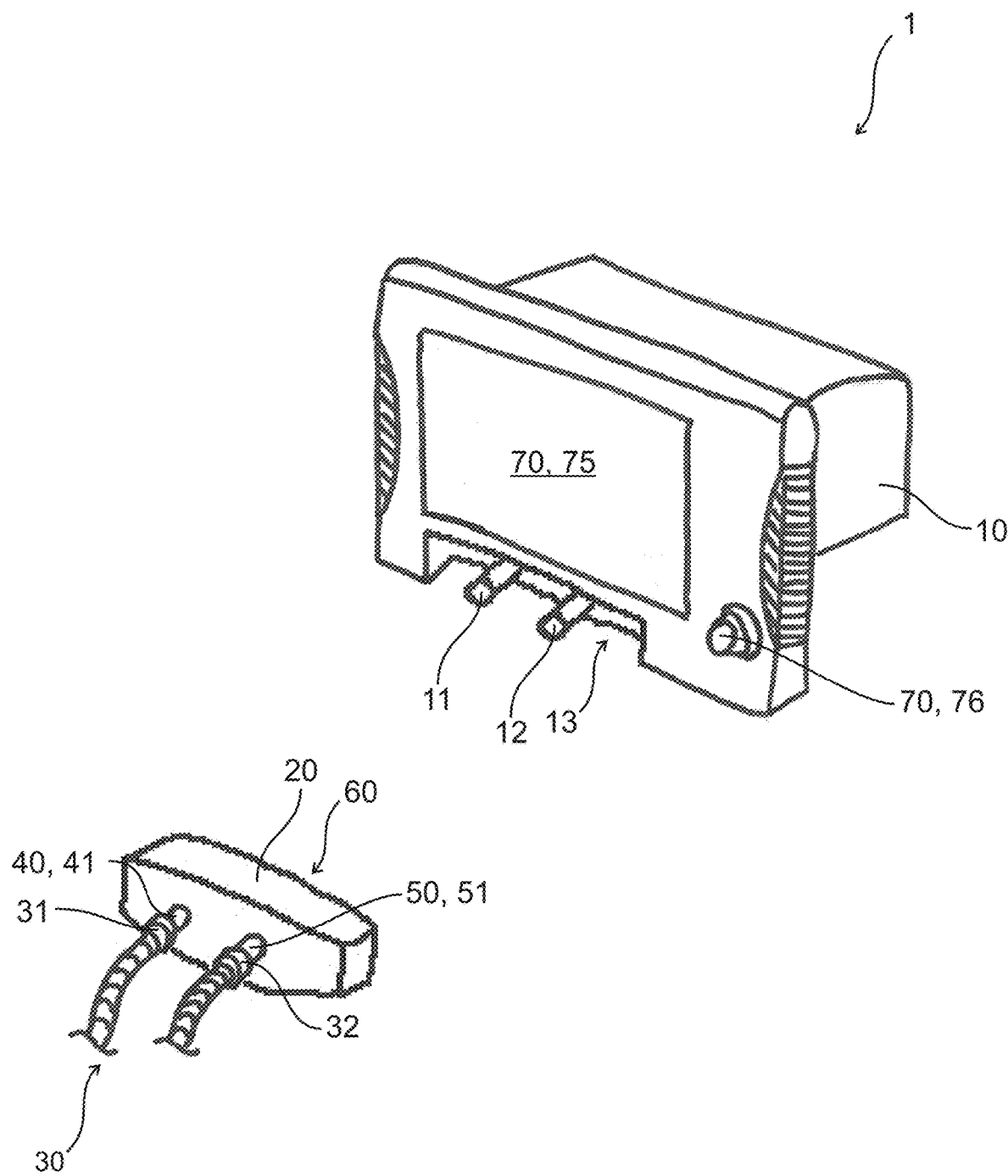
FIG. 6 is a perspective view a second possible embodiment of a ventilator according to the present invention.

Contrary to this, both the display element 75 of the data unit 70 and the input element 76 of the data unit 70 are configured as part of the ventilation unit 10 in the alternative embodiment of a ventilator 1 shown in FIG. 6. The transfer unit 20 is thus formed in this embodiment at least essentially by the elements of the breathing air port 40 as well as of the exhaled air section 50. The ventilation tube element 30, whose counter-patient inhalation port 31 is mounted at the patient inhalation port 41, as well as the counter-patient exhalation port 32, which is mounted at the patient exhalation port 51, are again shown as well. In addition, the counter-ventilation inhalation port 11 as well as the counter-ventilation exhalation port 12, which form parts of the counter-mounting section 13, are additionally also shown at the ventilation unit 10. This counter-mounting section 13 is configured especially such that it is configured for receiving the mounting section 60 of the transfer unit 20 in a positive-locking manner.

Figure 7:
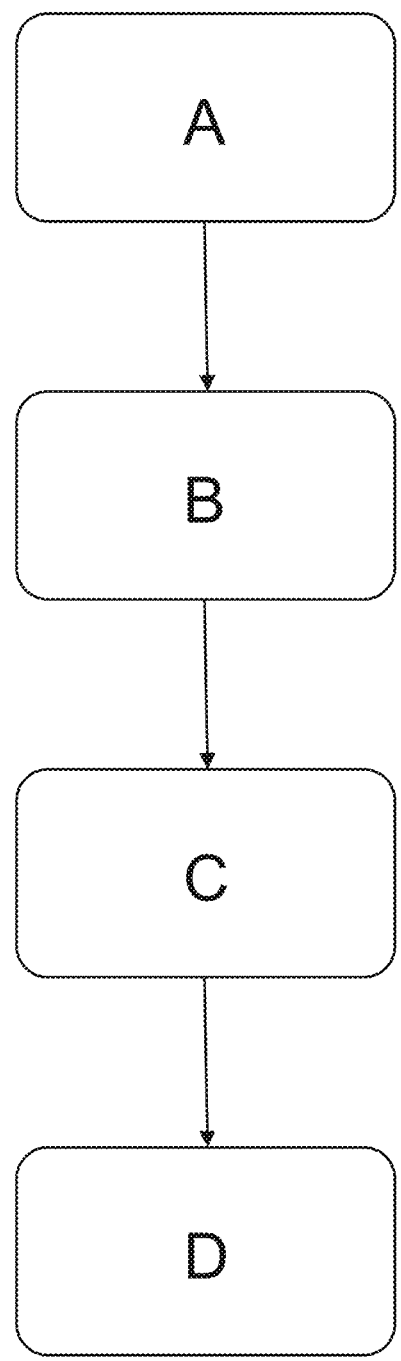
FIG. 7 is a flow diagram of a process according to the present invention.
Figure 8:
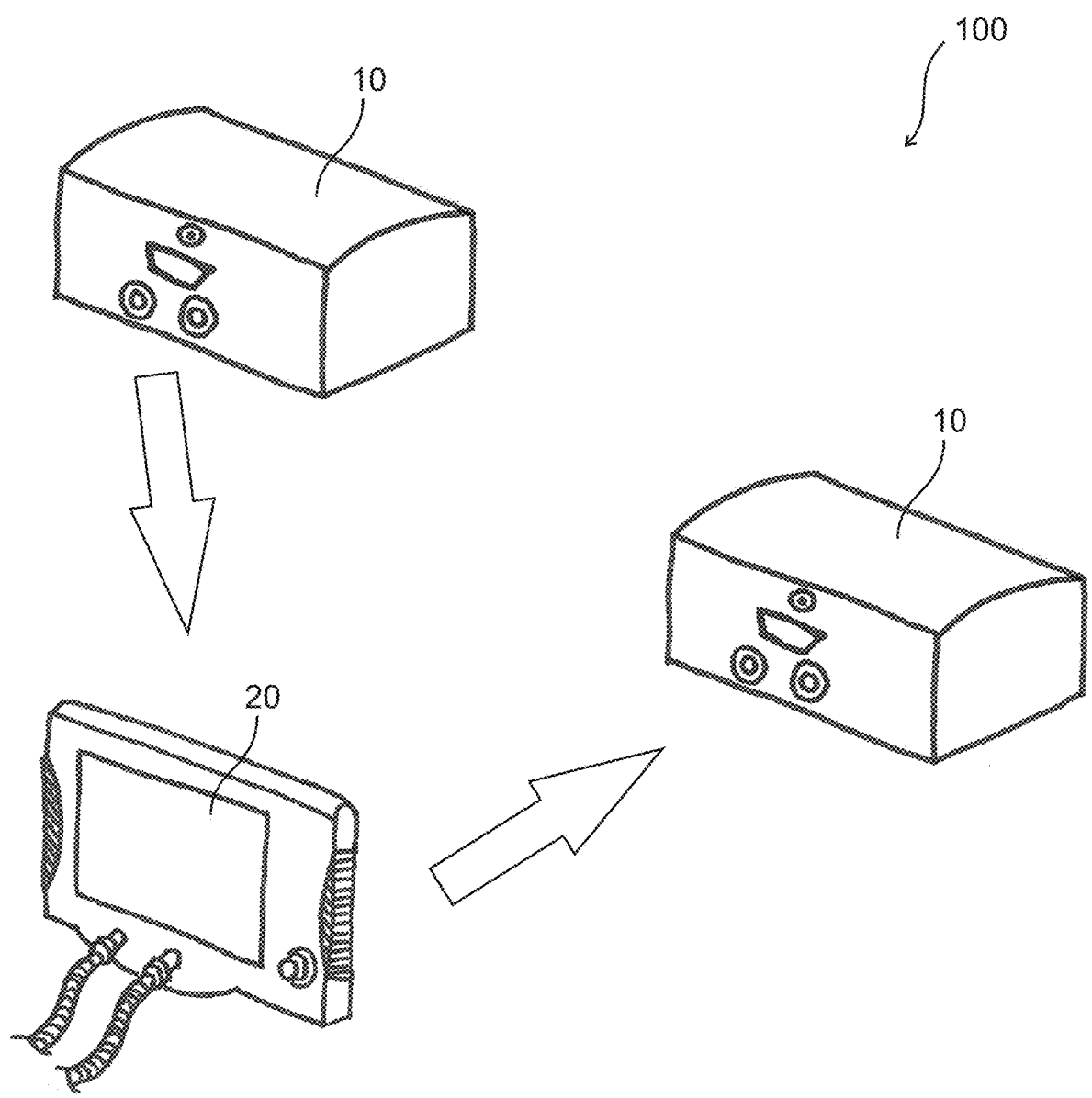
FIG. 8 is a perspective view of a ventilation system according to the present invention during the carrying out of a process according to the present invention.

FIG. 7 shows a process according to the present invention, in which steps a) through d) are each designated by uppercase characters. At the same time, FIG. 8 shows a ventilation system 100 according to the present invention in a state that is located between steps b) and c) of a process according to the present invention. The two figures will be described together below, and the respective details will be discussed separately. To increase clarity, only the ventilation system 100, the transfer unit 20 and the two ventilation units 10 are designated by reference numbers in FIG. 8 among the devices used.

A second ventilation unit 10 is put into a receiving mode in a first step a) of a process according to the present invention, designated by A in FIG. 7. In other words, the second ventilation unit 10, which is currently still unused, is put into a receiving mode in a ventilation system 100 according to the present invention with at least two ventilation units 10, wherein a transfer unit 20 is mounted at a first ventilation unit 10 and a first ventilator 1 is thus formed. A receiving mode in the sense of the present invention means especially that the second ventilation unit 10 is prepared or is such that a ventilation process can be started without delay after a transfer unit 20 has been mounted. In the next step b), designated by B in FIG. 7, the transfer unit 20 is now removed from the first ventilation unit 10. This step is shown upon its conclusion in FIG. 8. At the same time, an activation of the breathing valve 43 and of the exhalation valve 53 of the transfer unit 20 is carried out in step b). Continuation of the ventilation process of the patient is maintained at least such that a minimum pressure of an exhaled air 92 of the patient is maintained through the transfer unit 20. In other words, an end-expiratory pressure can be ensured in this manner for the patient. In the next step c), designated by C in FIG. 7, the transfer unit 20 is mounted again at the second ventilation unit 10, as a result of which a second ventilator 1 is formed. This is suggested in FIG. 8 by the arrow pointing towards the second ventilation unit 10. Provisions may be made already when removing the transfer unit 20 from the first ventilation unit 10 for the latter to be likewise put into a receiving mode. Should it not be possible to mount the transfer unit 20 at the second ventilation unit 10, the transfer unit 20 can be mounted again at the first ventilation unit 10 in an especially simple manner. Data related to the ventilation process of the patient can, for example, also be transmitted to a data unit 70, especially a memory element 72, and these data can be transmitted again to the second ventilation unit 10 especially after mounting the transfer unit 20 at the second ventilation unit 10. An especially interruption-free and reliable continuation of the ventilation process of the patient can be ensured in this manner. In the last step d), designated by D in FIG. 7, the receiving mode of the second ventilation unit 10 is ended after mounting the transfer unit 20 at the second ventilation unit 10 and the ventilation process by the second ventilator 1, which was formed just now, is started at the same time or at least essentially at the same time. A transfer of the transfer unit 20 from one ventilation unit 10 to the next ventilation unit 10, which transfer is especially simple, reliable and at the same time represents the least possible compromise for the patient, can be ensured in this manner. To make a process according to the present invention especially reliable, provisions may be made, in particular, for checking the feasibility of changing the ventilator 1 before step b), especially before step a). A result of this checking can be especially such that when a negative result is obtained, removal of the transfer unit 20 from the first ventilation unit 10 is prevented in the first place. The patient is prevented in this manner from being jeopardized by a needless compromise of the ventilation process.

While specific embodiments of the invention have been shown and described in detail to illustrate the application of the principles of the invention, it will be understood that the invention may be embodied otherwise without departing from such principles.

LIST OF REFERENCE NUMBERS

1 Ventilator
10 Ventilation unit
11 Counter-ventilation inhalation port
12 Counter-ventilation exhalation port
13 Counter-mounting section
14 Counter-data interface
15 Counter-energy interface
16 Pneumatic unit
17 Control unit
20 Transfer unit
30 Ventilation tube element
31 Counter-patient inhalation port
32 Counter-patient exhalation port
40 Breathing air section
41 Patient inhalation port
42 Ventilation inhalation port
43 Breathing valve
44 First nonreturn device
50 Exhaled air section
51 Patient exhalation port
52 Ventilation exhalation port
53 Exhalation valve
54 Second nonreturn device
55 Minimum pressure device
56 Setting element

What is claimed is:

1. A ventilator transfer unit for a ventilator that carries out a patient ventilation process, the transfer unit comprising:
   a mounting section for connectable and disconnectable reversible mounting at a counter-mounting section of a ventilation unit of the ventilator, wherein the mounting section comprises a locking device configured to reversibly and controllably fix the transfer unit at the ventilation unit;
   a breathing air guiding section for guiding breathing air; the breathing air guiding section comprising a patient inhalation port providing a fluid-communicating connection to a counter-patient inhalation port of a ventilation tube element and a ventilation inhalation port for fluid-communicating connection to a counter-ventilation inhalation port of the ventilation unit;
   an exhalation guiding section for guiding exhaled air, the exhalation guiding section comprising a patient exhalation port for a fluid-communicating connection to a counter-patient exhalation port of the ventilation tube element and a ventilation exhalation port for a fluid-communicating connection to a counter-ventilation exhalation port of the ventilation unit;
   a breathing valve comprising a first nonreturn device allowing a flow of breathing air with a breath flow direction from the ventilation inhalation port to the patient inhalation port, the first nonreturn device being mounted in the breathing air guiding section; and
   an exhalation valve comprising: a second nonreturn device allowing a flow of exhaled air with an exhalation flow direction from the patient exhalation port to the ventilation exhalation port, the second nonreturn device being mounted in the exhalation guiding section; and a minimum pressure device to establish a minimum pressure of the exhaled air with an exhalation flow direction in the exhalation guiding section, the minimum pressure device being mounted in the exhalation valve, the ventilation exhalation port extending about a portion of the minimum pressure device.

2. A ventilator transfer unit in accordance with claim 1, further comprising:
   a data unit with a data interface for a data-communicating connection to a counter-data interface of the ventilation unit, the locking device being located between the data interface and the patient exhalation port; and a memory element connected to the data interface in a data-communicating manner for storage of data comprising at least of:
- a ventilation parameter of the patient ventilation process;
- at least one measured variable;
- a target variable indicating the patient ventilation process and/or the ventilation parameter.

3. A ventilator transfer unit in accordance with claim 2, wherein the data unit comprises:
- at least one sensor element for determining measured data of the patient ventilation process; and
- a computer configured to analyze the measured data of the at least one sensor element and generate analysis results, wherein at least one of the measured data and the analysis results is stored in the memory element.

4. A ventilator transfer unit in accordance with claim 3, wherein the data unit further comprises a display element for displaying data stored in the memory element, the locking device being located between the display element and the ventilation exhalation port.

5. A ventilator transfer unit in accordance with claim 2, wherein the data unit comprises at least one of:
- an input element for setting the data unit for setting the data stored in the memory element;
- a sensor element;
- a computer;
- a display element; and
- an operating element.

6. A ventilator transfer unit in accordance with claim 1, wherein the locking device comprises a locking element for reversibly and controllably fixing the transfer unit at the ventilation unit.

7. A ventilator transfer unit in accordance with claim 6, wherein the locking device further comprises an operating element for establishing and/or releasing the fixation of the transfer unit at the ventilation unit.

8. A ventilator transfer unit in accordance with claim 6, wherein the locking element is configured as a mechanical and/or electromechanical and/or magnetic and/or pneumatic and/or hydraulic locking element.

9. A ventilator transfer unit in accordance with claim 1, further comprising an energy unit with a chargeable energy storage element for supplying the transfer unit with electrical energy.

10. A ventilator transfer unit in accordance with claim 9, wherein the energy unit further comprises an energy interface connected in an energy-communicating manner with the energy storage element for energy-communicating connection to a counter-energy interface of the ventilation unit for charging the energy storage element with electrical energy, the locking device being located between the energy interface and the patient exhalation port.

11. A ventilator transfer unit in accordance with claim 1, wherein the minimum pressure device comprises a pressure-controlled and/or electromechanical and/or mechanical setting element for setting the minimum pressure in the exhalation guiding section, the ventilation exhalation port comprising a ventilation exhalation port interior space, the portion of the minimum pressure device being arranged in the ventilation exhalation port interior space.

12. A ventilator for carrying out a patient ventilation process, the ventilator comprising:
- a ventilation unit comprising a pneumatic unit for carrying out the patient ventilation process;
- a control unit configured to control operation of the pneumatic unit; and
- a transfer unit comprising:
  - a mounting section for connectable and disconnectable reversible mounting at a counter-mounting section of a ventilation unit of the ventilator, wherein the mounting section comprises a locking device configured to reversibly and controllably fix the transfer unit at the ventilation unit;
  - a breathing air guiding section for guiding breathing air; the breathing air guiding section comprising a patient inhalation port providing a fluid-communicating connection to a counter-patient inhalation port of a ventilation tube element and a ventilation inhalation port for fluid-communicating connection to a counter-ventilation inhalation port of the ventilation unit;
  - an exhalation guiding section for guiding exhaled air, the exhalation guiding section comprising a patient exhalation port for a fluid-communicating connection to a counter-patient exhalation port of the ventilation tube element and a ventilation exhalation port for a fluid-communicating connection to a counter-ventilation exhalation port of the ventilation unit;
  - a breathing valve comprising a first nonreturn device allowing a flow of breathing air with a breath flow direction from the ventilation inhalation port to the patient inhalation port, the first nonreturn device being mounted in the breathing air guiding section; and
  - an exhalation valve comprising: a second nonreturn device allowing a flow of exhaled air with an exhalation flow direction from the patient exhalation port to the ventilation exhalation port, the second nonreturn device being mounted in the exhalation guiding section;
  - and a minimum pressure device to establish a minimum pressure of the exhaled air with an exhalation flow direction in the exhalation guiding section, the minimum pressure device being mounted in the exhalation valve, the ventilation exhalation port extending about a portion of the minimum pressure device, wherein a mounting section of the transfer unit is mounted reversibly at a counter-mounting section of the ventilation unit, whereby the ventilation inhalation port of the transfer unit is fluid-communicatingly connected to the counter-ventilation inhalation port of the ventilation unit, and whereby the ventilation exhalation port of the transfer unit is fluid-communicatingly connected to a counter-ventilation exhalation port of the ventilation unit.

13. A ventilator in accordance with claim 12, wherein the ventilation unit is configured as a stationary ventilation unit and/or as a mobile ventilation unit, the ventilation exhalation port comprising a ventilation exhalation port interior space, the portion of the minimum pressure device being arranged in the ventilation exhalation port interior space.

14. A ventilator in accordance with claim 12, wherein the control unit is integrated into the transfer unit and/or into the ventilation unit.

15. A ventilator in accordance with claim 12, wherein:
- the transfer unit further comprises a data interface and the ventilation unit further comprises a counter-data interface and the data interface is data-communicatingly connected to the counter-data interface; or
- the transfer unit further comprises an energy interface and the ventilation unit comprises a counter-energy interface and the energy interface is energy-communicatingly connected to the counter-energy interface; or the transfer unit further comprises a data interface and an energy interface and the ventilation unit further comprises a counter-data interface and a counter-energy interface and both the data interface is data-communicatingly connected to the counter-data interface and the energy interface is energy-communicatingly connected to the counter-energy interface.

16. A ventilator in accordance with claim 12, wherein the ventilation unit and the transfer unit further comprise at least one of:
a display element for displaying data, the locking device being located between the display element and the ventilation exhalation port; and
an input element for an input of settings to at least one of the transfer unit and the ventilation unit, the locking device being located between the input element and the ventilation exhalation port.

17. A ventilation system for carrying out a patient ventilation process, the ventilation system comprising:
a transfer unit comprising:
a mounting section for connectable and disconnectable reversible mounting at a counter-mounting section of a ventilation unit, wherein the mounting section comprises a locking device configured to reversibly and controllably fix the transfer unit at the ventilation unit;
a breathing air guiding section for guiding breathing air; the breathing air guiding section comprising a patient inhalation port providing a fluid-communicating connection to a counter-patient inhalation port of a ventilation tube element and a ventilation inhalation port for fluid-communicating connection to a counter-ventilation inhalation port of the ventilation unit;
an exhalation guiding section for guiding exhaled air, the exhalation guiding section comprising a patient exhalation port for a fluid-communicating connection to a counter-patient exhalation port of the ventilation tube element and a ventilation exhalation port for a fluid-communicating connection to a counter-ventilation exhalation port of the ventilation unit;
a breathing valve comprising a first nonreturn device allowing a flow of breathing air with a breath flow direction from the ventilation inhalation port to the patient inhalation port, the first nonreturn device being mounted in the breathing air guiding section; and
an exhalation valve comprising: a second nonreturn device allowing a flow of exhaled air with an exhalation flow direction from the patient exhalation port to the ventilation exhalation port, the second nonreturn device being mounted in the exhalation guiding section; and a minimum pressure device to establish a minimum pressure of the exhaled air with an exhalation flow direction in the exhalation guiding section, the minimum pressure device being mounted in the exhalation valve, the ventilation exhalation port extending about a portion of the minimum pressure device, wherein a mounting section of the transfer unit is mounted reversibly at a counter-mounting section of the ventilation unit, whereby the ventilation inhalation port of the transfer unit is fluid-communicatingly connected to the counter-ventilation inhalation port of the ventilation unit, and whereby the ventilation exhalation port of the transfer unit is fluid-communicatingly connected to a counter-ventilation exhalation port of the ventilation unit; and
at least two ventilation units, the at least two ventilation units each comprising: at least one pneumatic unit for carrying out the patient ventilation process; the counter-mounting section for reversibly mounting the mounting section of the transfer unit; the counter-ventilation port for fluid-communicating connection to the ventilation inhalation port of the transfer unit; and the counter-ventilation exhalation port for fluid-communicating connection to the ventilation exhalation port of the transfer unit, wherein the transfer unit is mountable reversibly at each of the at least two ventilation units to form a ventilator therewith.

18. A process for changing a ventilator, the process comprising:
providing a transfer unit comprising: a mounting section for connectable and disconnectable reversible mounting at a counter-mounting section of a ventilation unit, wherein the mounting section comprises a locking device configured to reversibly and controllably fix the transfer unit at the ventilation unit; a breathing air guiding section for guiding breathing air; the breathing air guiding section comprising a patient inhalation port providing a fluid-communicating connection to a counter-patient inhalation port of a ventilation tube element and a ventilation inhalation port for fluid-communicating connection to a counter-ventilation inhalation port of the ventilation unit; an exhalation guiding section for guiding exhaled air, the exhalation guiding section comprising a patient exhalation port for a fluid-communicating connection to a counter-patient exhalation port of the ventilation tube element and a ventilation exhalation port for a fluid-communicating connection to a counter-ventilation exhalation port of the ventilation unit; a breathing valve comprising a first nonreturn device allowing a flow of breathing air with a breath flow direction from the ventilation inhalation port to the patient inhalation port, the first nonreturn device being mounted in the breathing air guiding section; and an exhalation valve comprising: a second nonreturn device allowing a flow of exhaled air with an exhalation flow direction from the patient exhalation port to the ventilation exhalation port, the second nonreturn device being mounted in the exhalation guiding section; and a minimum pressure device to establish a minimum pressure of the exhaled air with an exhalation flow direction in the exhalation guiding section, the minimum pressure device being mounted in the exhalation valve, the ventilation exhalation port extending about a portion of the minimum pressure device, wherein a mounting section of the transfer unit is mounted reversibly at a counter-mounting section of the ventilation unit, whereby the ventilation inhalation port of the transfer unit is fluid-communicatingly connected to the counter-ventilation inhalation port of the ventilation unit, and whereby the ventilation exhalation port of the transfer unit is fluid-communicatingly connected to a counter-ventilation exhalation port of the ventilation unit;
providing at least two ventilation units, the at least two ventilation units each comprising: at least one pneumatic unit for carrying out the patient ventilation process; the counter-mounting section for reversibly mounting the mounting section of the transfer unit; the counter-ventilation port for fluid-communicating connection to the ventilation inhalation port of the transfer unit; and the counter-ventilation exhalation port for fluid-communicating connection to the ventilation exhalation port of the transfer unit, wherein the transfer unit is mountable at a first ventilation unit of the at least two ventilation units for forming a first ventilator and the transfer unit is mountable at a second ventilation unit of the at least two ventilation units for forming a second ventilator;

mounting the transfer unit at the first ventilation unit to form the first ventilator;

carrying out the patient ventilation process by the first ventilator;

putting of the second ventilation unit into a receiving mode;

removing the transfer unit from the first ventilation unit, wherein the removing comprises an activation of the breathing valve and of the exhalation valve of the transfer unit;

mounting of the transfer unit at the second ventilation unit to form the second ventilator; and ending the receiving mode of the second ventilation unit and starting the patient ventilation process by the second ventilator.

19. A process in accordance with claim 18, wherein first ventilation unit is put into the receiving mode after removal of the transfer unit from the first ventilation unit, and the receiving mode of the first ventilation unit is ended.

20. A process in accordance with claim 18, wherein prior to removing the transfer unit from the first ventilation unit, wherein the removing comprises an activation of the breathing valve and of the exhalation valve of the transfer unit carrying out at least one of the steps comprising:

transmitting data from the from the first ventilation unit to a memory element of the transfer unit, the data comprising at least one ventilation parameter of the patient ventilation process and/or at least one measured variable and/or a target variable indicating the patient ventilation process and/or a ventilation parameter;

charging an energy storage element of the transfer unit by the first ventilation unit; and actuating a setting element of a minimum pressure device of the exhalation valve of the transfer unit for setting a minimum pressure in the exhalation guiding section.

21. A process in accordance with claim 20, wherein data stored in the memory element are transmitted at least partly to the second ventilation unit during the step of mounting of the transfer unit at the second ventilation unit and/or during the step of ending the receiving mode of the second ventilation unit and starting the patient ventilation process by the second ventilator.

22. A process in accordance with claim 18, wherein:

the provided ventilation units and the transfer unit further comprise a locking device for the reversible and controllable fixation of the transfer unit at the respective ventilation unit; and a feasibility of a ventilator change is checked before the step of removing the transfer unit from the first ventilation unit, wherein the removing comprises an activation of the breathing valve and of the exhalation valve of the transfer unit and removal of the transfer unit from the first ventilation unit is prevented by blocking the locking device in case of a negative result of the checking.

\* \* \* \* \*